US011206995B2

(12) United States Patent
Srinivasan

(10) Patent No.: US 11,206,995 B2
(45) Date of Patent: Dec. 28, 2021

(54) SAFE INFANT MR IMAGING SYSTEM

(71) Applicant: Advanced Imaging Research, Inc., Cleveland, OH (US)

(72) Inventor: Ravi Srinivasan, Beachwood, OH (US)

(73) Assignee: ADVANCED IMAGING RESEARCH, INC., Cleveland, OH (US)

(*) Notice: Subject to any disclaimer, the term of this patent is extended or adjusted under 35 U.S.C. 154(b) by 310 days.

(21) Appl. No.: 15/560,328

(22) PCT Filed: Mar. 23, 2015

(86) PCT No.: PCT/US2015/021938
§ 371 (c)(1),
(2) Date: Sep. 21, 2017

(87) PCT Pub. No.: WO2016/153471
PCT Pub. Date: Sep. 29, 2016

(65) Prior Publication Data
US 2018/0064365 A1 Mar. 8, 2018

(51) Int. Cl.
*A61B 5/055* (2006.01)
*G01R 33/3815* (2006.01)
(Continued)

(52) U.S. Cl.
CPC .............. *A61B 5/055* (2013.01); *A61G 11/00* (2013.01); *A61G 11/005* (2013.01);
(Continued)

(58) Field of Classification Search
CPC .............. A61B 5/0555; A61B 2503/04; A61B 5/055; A61B 2503/045; A61B 2017/00911;
(Continued)

(56) References Cited

U.S. PATENT DOCUMENTS 4,672,346 A * 6/1987 Miyamoto .............. B29C 67/20
335/296
5,696,476 A * 12/1997 Havens .............. G01R 33/3873
324/318
(Continued)

FOREIGN PATENT DOCUMENTS

CN 202196164 4/2012
EP 1519390 A2 3/2005
(Continued)

OTHER PUBLICATIONS

International Search Report and Written Opinion for International Application No. PCT/US2015/021938, dated Jun. 2, 2015.
(Continued)

*Primary Examiner* — Christopher Koharski
*Assistant Examiner* — Amy J Shafqat
(74) *Attorney, Agent, or Firm* — Kusner & Jaffe

(57) ABSTRACT

A pediatric magnetic resonance imaging (MRI) system includes a magnet (9), an isolette (14) including a patient section for accommodating a patient, the isolette positionable relative to the magnet; and a radio frequency (RF) array (10) positionable within the patient section of the isolette (14). The RF array (10) includes a plurality of coils configured for simultaneous imaging of different portions of a patient, the plurality of coils being distinct from one another.

19 Claims, 10 Drawing Sheets

(51) Int. Cl.
*G01R 33/28* (2006.01)
*G01R 33/34* (2006.01)
*A61G 11/00* (2006.01)

(52) U.S. Cl.
CPC ..... *G01R 33/288* (2013.01); *G01R 33/34046* (2013.01); *G01R 33/3815* (2013.01); *A61B 2503/04* (2013.01); *A61G 11/006* (2013.01); *A61G 11/009* (2013.01); *A61G 2203/20* (2013.01); *A61G 2210/50* (2013.01)

(58) Field of Classification Search
CPC ........... A61G 11/005; A61G 11/009; A61G 2203/20; A61G 2210/50; A61G 11/006; A61G 11/00; A61G 12/00; A61G 12/002; A61G 12/008; G01R 33/288; G01R 33/34046; G01R 33/3815; G01R 33/383; G01R 33/381; G01R 33/385; G01R 33/465; G01R 33/30; G01R 33/34; G01R 33/3806; H01F 6/00; H01F 7/202; H01F 7/204; A61M 2202/03; A61F 7/00; A61F 7/0053

See application file for complete search history.

(56) References Cited

U.S. PATENT DOCUMENTS

| | | | |
|---|---|---|---|
| 6,241,671 B1 * | 6/2001 | Ritter ............... | A61B 34/70 600/427 |
| 10,383,762 B2 * | 8/2019 | Rapoport ........... | A61G 11/00 |
| 2002/0173717 A1 | 11/2002 | Rohling et al. | |
| 2004/0116799 A1 | 6/2004 | Srinvasan | |
| 2005/0062473 A1 * | 3/2005 | Ryan ................. | H01F 6/04 324/318 |
| 2005/0107686 A1 * | 5/2005 | Chan ................. | G01R 33/3415 600/422 |
| 2005/0113668 A1 | 5/2005 | Srinvasan | |
| 2006/0012369 A1 * | 1/2006 | Neufeld ............ | G01R 33/34046 324/318 |
| 2006/0255805 A1 * | 11/2006 | Crozier ............. | G01R 33/381 324/318 |
| 2007/0108979 A1 | 5/2007 | Ryan et al. | |
| 2007/0232894 A1 * | 10/2007 | Feenan .............. | A61B 5/055 600/410 |
| 2008/0231277 A1 * | 9/2008 | Yamamoto ......... | G01R 33/307 324/318 |
| 2010/0315085 A1 * | 12/2010 | Brown .............. | G01R 33/34084 324/309 |
| 2012/0126814 A1 * | 5/2012 | Fischer ............. | G01R 33/30 324/318 |
| 2012/0134924 A1 * | 5/2012 | Cerwin .............. | A61K 41/0028 424/9.1 |
| 2012/0265052 A1 | 10/2012 | Rohr et al. | |
| 2013/0085373 A1 | 4/2013 | Yang et al. | |
| 2016/0089055 A1 * | 3/2016 | Rapoport .......... | A61G 11/00 600/415 |
| 2016/0225504 A1 * | 8/2016 | Hori ................. | A61B 5/0555 |
| 2018/0153435 A1 * | 6/2018 | Rapoport .......... | A61B 5/0036 |
| 2019/0328596 A1 * | 10/2019 | Rapoport .......... | A61B 5/0036 |

FOREIGN PATENT DOCUMENTS

| | | |
|---|---|---|
| WO | WO 9848756 | 11/1998 |
| WO | WO 2014188426 A1 | 11/2014 |

OTHER PUBLICATIONS

Office Action dated Jul. 17, 2020 from related/corresponding European Patent Appl. No. 15714746.3, filed Oct. 6, 2017.
Parkinson et al, "Development of a Cryogen Free 1.5 T YBCO HTS Magnet for MRI," IEEE Transactions on Applied Superconductivity, vol. 23, No. 3, Jun. 2013.

* cited by examiner

SAFE INFANT MR IMAGING SYSTEM

RELATED APPLICATION DATA

This application is a National Stage of international application no. PCT/US2015/021938, filed on Mar. 23, 2017 is incorporated herein by reference in its entirety.

TECHNICAL FIELD

The present disclosure relates to magnetic resonance imaging systems and, more particularly, to an advanced isolette imaging system that provides high-resolution imaging.

BACKGROUND OF THE INVENTION

Infants who need special care are placed in a specialized area, such as a neonatal intensive care unit (NICU), pediatric infant care unit (PICU), cardiac intensive care unit (CICU), etc. within a hospital. Premature sick newborns with compromised thermoregulatory systems demanding special environment are kept in a warm isolette at air temperatures anywhere between 25 to 39 degrees Celcius as prescribed by a physician. Infants with a compromised cardio-pulmonary system and those with respiratory illness incapable of breathing entirely on their own are supported with artificial ventilation systems. Likewise infants who cannot maintain electrolyte balance and/or require nutrition are assisted with infusion devices with constant flow rates to support life. Vital sign parameters such as saturated pulse-oximetry, echocardiogram (ecg), electroencephalographs (eeg), end tidal carbondioxide, non-invasive and sometimes invasive blood pressure, skin temperature etc., are continuously measured to observe patient status and response to therapy or intervention.

Traditional hospital equipment and accessories for infants are not magnetic resonance compatible as the equipment is costly and the volume of pediatric radiology procedures is generally low. However this is changing rapidly, as more infants undergo radiology procedures much earlier in life to minimize burden to the infant and society as these infants age. Nevertheless, sick infants have to be transported to other departments and caregivers accompany the infants, which leaves the unit with fewer caregivers.

Intra-hospital or sometimes inter-hospital transport is very stressful to the infant, caregivers and parents. Due to safety issues related to infant transport, delicate infants who demand immediate special care may be left in the NICU and are not transported to other hospital sections for non-invasive imaging-based diagnostic procedures. In such situations, injury to the infant's brain or major organs may have time to manifest, which is undesirable. Diagnosis and follow-up patient care is generally limited to mild and some moderately ill infants, and is not generally extended to severely ill infants.

Magnetic resonance (MR) imaging is a safe, non-ionizing radiation-based diagnostic imaging tool that is routinely used in the characterization of illnesses of the brain, heart or major organs in the torso (liver, kidney, spleen, pelvis, etc.). Pediatric MRI involves transport of sick infants followed by the diagnostic procedure. Remote MRI procedures have unique constraints adding burden to the caregiver, which makes pediatric MRI unpopular amongst radiographers. The lack of comfort expressed by the clinical caregiver in transferring the sick pediatric patient can lead to compromising care and handling of adverse situations remote from the respective clinical unit. Further reduction of skilled caregivers in the clinical unit as a result of patient transfers seeking diagnosis (including the sometimes long diagnostic procedure) can be overwhelming.

Diagnosis depends on MR image quality. Better image quality permits clear delineation of diseased versus normal tissue, which in turn can lead to prompt therapy, intervention or follow-up response to therapy. Since signal-to-noise ratio (SNR) is proportional to filling factor (filling factor is defined as the volume of anatomy to that of the imaging device), generally smaller anatomies will have a low filling factor and thus a lower SNR. To obtain higher imaging resolutions for small anatomies requires repeat scans, which prolongs the MRI exam. Further, "motional" artifacts in longer MRI exams are likely, which necessitates repeat exams and thus further prolonging the MRI exam. This is especially true when the imaging devices are placed "around" an isolette that is dimensioned to furnish uniform air flow over the patient.

Reducing the size of the isolette, however, may not provide sufficient room to maintain uniform air flow including room for patient connections to life-sustaining devices, e.g., endo-tracheal tube or breathing circuits connected to the ventilator, etc. and physiological vital signs monitoring equipment such as pulseoximeter, ecg, non-invasive blood pressure, end tidal $CO_2$ equipment etc. Thus, the isolette should be proportionately sized to meet or exceed performance and other safety standards without compromising care. Doing so, however, results in moving the imaging device away from the target imaging volume, resulting in lower SNR.

Infants born with a congenital anomaly and/or those slated for surgery require multiple MRI studies be performed in one clinical setting. Such studies enable evaluation of different strategies for minimally invasive surgery and evaluation brain development post surgery to predict neurodevelopment and measure or predict cardiovascular outcome. Multiple studies are carried out by one or more coils to image the brain and heart, where the patient is moved after each study. Moving the fragile infant for performing multiple studies can be deleterious to the patient and increase the risk of contamination as well as the risk of dislodging life sustaining and monitoring lines, etc.

There is an unmet need to provide point-of-care safe MRI diagnosis and improve SNR to obtain higher imaging resolutions over smaller anatomies in a shorter scan time to aid diagnosis while minimizing patient time outside of the conventional incubator environment. In addition there is an unmet need to perform multiple studies in one clinical setting with high SNR coils with the need to move the patient.

SUMMARY OF THE INVENTION

An imaging system in accordance with the present disclosure provides a custom adaptable isolette system, high signal to noise imaging devices, and safe diagnostic imaging equipment best suited to provide "point of care diagnosis" for sick infants, without compromising safety of the infant, user or equipment. In this regard, the present disclosure provides a safe infant isolette that is virtually free from its placement location relative to a magnet of a magnetic resonance imaging system, and adapts to the ambient environment to precisely control temperatures within the isolette. The isolette includes life sustaining and monitoring equipment and accessories that do not significantly compromise equipment performance yet enhance patient, user and equipment safety. The imaging system includes high signal to noise imaging devices configured for use with the isolette and capable of producing enhanced image quality on smaller anatomies, and a magnet diagnostic imaging system having advanced magnet design to improve overall safety. Further, the magnetic diagnostic imaging system may be shielded to curtail fringe magnetic fields to acceptable levels at safe distances from the MRI magnet, thus permitting "point of care' diagnostics in or near the clinical department.

According to one embodiment, a pediatric magnetic resonance imaging (MRI) system includes: a magnet; an isolette including a patient section for accommodating a patient, the isolette positionable relative to the magnet; and a radio frequency (RF) array positonable within the patient section of the isolette, the RF array comprising a plurality of coils configured for simultaneous imaging of different portions of a patient, the plurality of coils being distinct from one another.

According to one embodiment, the magnet comprises wire formed from magnesium diboride ($MgB_2$).

According to one embodiment, the RF array includes: a support section for supporting a patient to be imaged; a gantry movably coupled to the support section; and a first coil of the plurality of coils is coupled to the gantry, the first coil, via the gantry, movable relative to the support section in at least two degrees of freedom.

According to one embodiment, the first coil is movable along a longitudinal axis of the support section.

According to one embodiment, the first coil is movable in elevation relative to the support section.

According to one embodiment, a second coil of the plurality of coils is arranged within the support section.

According to one embodiment, the support section includes an enclosed portion for receiving a head of the patient, the enclosed portion including a third coil for imaging a head of a patient.

According to one embodiment, the system includes a cooling system for controlling a temperature of the wire.

According to one embodiment, the cooling system is operative to maintain a temperature of the wire between 8-12 degrees K.

According to one embodiment, the cooling system comprises a conduction cooling system.

According to one embodiment, the cooling system is substantially cryogen-free.

According to one embodiment, a diameter of an inner bore of the magnet is greater than or equal to 56 cm and less than or equal to 70 cm.

According to one embodiment, an outer diameter of the magnet is greater than or equal to 120 cm and less than or equal to 150 cm.

According to one embodiment, the RF array comprises a high-permittivity material.

According to one embodiment, the high-permittivity material has a permitivitty between 200 and 2000.

According to one embodiment, a conductivity of the high-permitivitty material is substantially 0.

According to one embodiment, an RF transmit field of the RF array is substantially confined within a volume within the RF array.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

In the annexed drawings, like references indicate like parts or features.

DEFINITIONS

Figure 1:
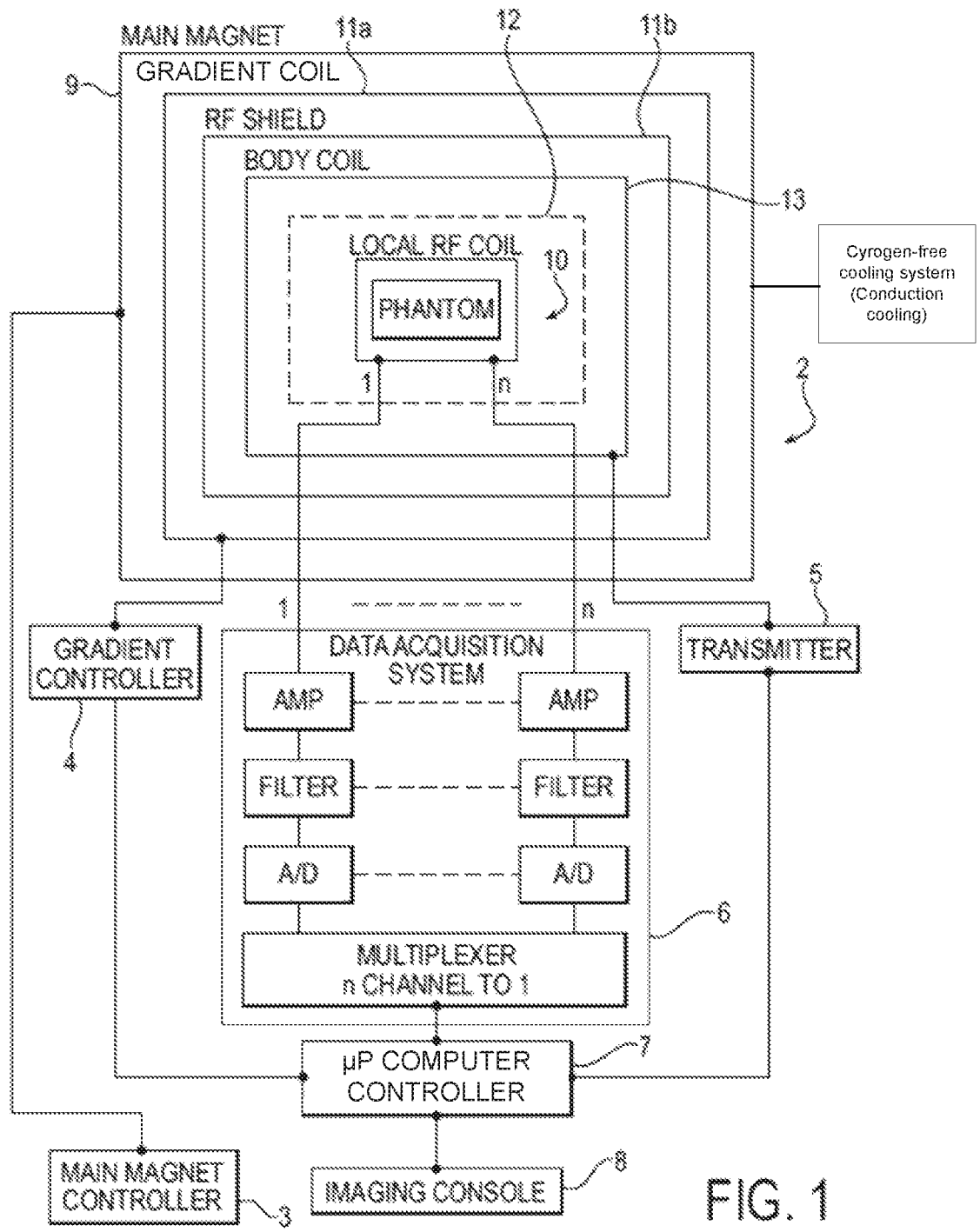
FIG. 1 is a block diagram of an exemplary MR system.

The term "infant" (Latin word infans, meaning unable to speak or speechless) relates to a newborn baby, premature baby or otherwise small baby generally from birth up to one year in age.

The term "radiology procedure" relates to non-invasive, resonance and non-resonance based imaging tools used for diagnosis and prognosis of illnesses.

The term "magnetic resonance" relates to techniques associated with anatomy, morphology, blood flow, biochemical properties, etc., including imaging, angiography, spectroscopy of the water proton and other metabolites such as phosphorous, sodium, lithium, etc. exhibiting magnetic resonance property.

The term "transport" relates to safely moving an infant along with life sustaining equipment and monitoring tools.

The term "modular system" relates to a system in which individual components can be quickly assembled and disassembled for ease of installation, de-installation, service, trouble shooting, design constraints, usability, etc.

The term "sub-system" relates generally to a subset of the infant isolette imaging system, mainly the infant isolette imaging system without the main diagnostic imaging equipment.

DESCRIPTION

Throughout this disclosure reference is made to MR compatible components, e.g., an MR compatible monitor or an MR compatible ventilator. Details on fabricating and/or modifying such components for compatibility with MR are provided in U.S. patent application Ser. No. 10/723,325 filed Nov. 26, 2003 and titled IMPROVED COMPATIBILITY OF ACCESSORY OF MAGNETIC RESONANCE, which is incorporated by reference herein. Accordingly, details regarding preparation of a component or components for MR compatibility will not be discussed in detail herein.

Briefly, interference with static magnetic fields can be reduced or eliminated by using non-interference generating components, such as non-magnetic components and/or non-conductive, non-metallic plastic components. These types of components do not produce a water signal, have very little or no ground leakage electrical currents (below 500 microamperes), and very little or no eddy currents. Thus, artifacts due to the components can be reduced and/or eliminated. For example, circulating currents within the components that can come in contact with the subject can be eliminated through the use of non-conductive materials, which are intended to enhance patient safety.

Additionally, the components should be transparent to the main magnetic field of the MR system. Metal components should be non-magnetic (e.g., strontium, phosphor-bronze, beryllium-copper, copper, aluminum, silver, gold etc.) and preferably have a low permeability, e.g., a permeability that will cause less than 1 percent eddy currents, ghosting and/or distortion of the image in all three axis X, Y, Z, respectively, particularly in low signal to noise scans with echo times less than 2.0 milliseconds. In most cases, diamagnetic and ferromagnetic materials should be limited, and in some cases diamagnetic and ferro-magnetic materials should not be used.

Interference due to time varying gradient magnetic fields can be reduced using intermediate frequency (IF) filters. For example, IF filters and feed-thru capacitors can be placed in all signal lines (e.g., data carrying lines), wherein the feed-thru capacitors either block all of the interferences or shunt them to ground. Additionally, gradient interferences can be minimized by reducing the size of the metals used in shielding the isolette electronics or by keeping them away from the gradient field of view (FOV). Ghosting or aliasing can be minimized by eliminating moving metal parts and by placing the metal sections away from the gradient crossovers along the magnet axis.

RF interference can be minimized by appropriate filtering mechanisms in passive signal lines and the active lines (lines that carry power). RF chokes can be used to prevent RF leakage, whereas high power RF filters capable of carrying a few amperes with very high impedances can be utilized.

Referring to FIG. 1, a block diagram of an MR system 2 that can be used in conjunction with an imaging sub-system in accordance with the present disclosure is shown. The MR system 2 includes a main magnet controller 3, a gradient controller 4, a transmitter 5 and a data acquisition system 6, as is conventional. A computer controller 7 controls the operation of the system, and system data is provided to a user through an imaging console 8. A local radiofrequency (RF) coil 10 of a neonate imaging sub-system 12 sends and receives data to/from the data acquisition system 6. A magnet 9 provides a magnetic field used during the imaging process, while gradient coil 11a and RF shield 11b enable enhanced imaging.

Magnet

In superconducting magnets liquid helium and nitrogen are used to cool the magnet to reduce total wire resistance. Such cooling enables creation of a steady magnetic field on the order of 1-10 Tesla. Adult sized magnets require roughly 1,000-2,000 liters of liquid helium to cool the magnet, which increases overall magnet dimension, weight and affects siting considerations. Liquid nitrogen is used to cool the liquid helium.

For a given magnetic field, important considerations include the choice of wire employed in the magnet (the wire preferably having good current carrying capacity at the temperature of operation (degrees Kelvin) and manageable hoop stress for a given stored energy). The use of high current carrying wire requires fewer turns (and possibly smaller footprint) to generate the same field strength at a magnet isocenter when compared to magnets using low current carrying wire. The higher the isocenter magnetic field the higher the SNR (SNR is proportional to the main magnet field strength B0) and therefore it can be advantageous to use high current carrying wire for the magnet 9.

The MRI system in accordance with the present disclosure includes a substantially helium-free (e.g., cryogenic free), pediatric sized, self-shielded superconducting main magnet 9. As used herein, substantially helium-free means that a cooling system of the magnet uses less than 20 liters of helium. Preferably, the magnet 9 has a warm bore internal diameter of 50-70 cm, an outer diameter of 100-150 cm and a length of 92 cm. The magnet 9 preferably is made of magnesium diboride ($MgB_2$) wire that via conduction cooling can operate at around 8-12 degrees Kelvin. This is in contrast to conventional niobium-titanium (NbTi) based magnets, which operate around 4.2 degrees Kelvin on adult sized magnets. Further, in NbTi based magnets the hoop stress on the wires for a given stored energy is greater than the hoop stress on corresponding $MgB_2$ wire. Such increased hoop stress could possibly quench the magnet with slight instability, and could compromise safety, which is undesirable.

Adult sized magnets have large fringe fields and can pose a hazard due to interference with other equipment. Use of smaller magnets for pediatric patients in accordance with the present disclosure will bring risks to acceptable levels. Further, use of cryogenic-free magnets with superconducting wire technology employing novel magnesium-boron and the like alloy (e.g., magnesium diboride, $MgB_2$) enables operation at higher temperatures. By allowing operation at higher temperatures, the cryogenic (helium) chamber can be eliminated and thus the size and weight of the magnet 9 can be reduced. This can further reduce the MRI foot print and ease siting considerations within a hospital complex.

More particularly, a pediatric magnet 9 as set forth above can have a current carrying density of around 600A/$mm^2$ ($J_c$) and operate at elevated temperatures as mentioned above. Additionally, a field on the magnet wire, stored energy in the magnet (est. 6-8 MJ), hoop stress, etc. for the magnet 9 provides a main magnetic field strength of about 3 Tesla at the magnet isocenter. With improvements in the manufacturing process this limit can be raised.

A five gauss line extending radially from the magnet 9 is estimated to be less than and axially around two meters from the magnet bore. As a result, the magnet 9 can be installed in a 12'×15' floor space without posing interference to neighboring rooms in a hospital building. Estimated magnet weight of around 900-1,100 Kgs distributed over a 15 ft$^2$ floor space is suited for any hospital floor (generally >100 Kg/ft$^2$) without requiring additional reinforcement. A passive shim liner with 16-32 symmetric trays can extend from front to the back of the magnet lines inside of the main magnet bore (not shown).

The magnet 9 can include a set of epoxy potted, water cooled "thumb print" minimum inductance gradient coil set 11a as is conventional along with a very fine copper RF screen 18 (~5 microns). The RF screen (shield) 11b further encompasses a whole body transmit coil 13 that can be driven in a single channel, circularly-polarized quadrature mode in two or more points or driven in two or more channels to support parallel transmit. A single channel can be split in to multiple channels using an amplitude-phase controlled solid-state power splitter or, for example, using a Butler matrix (see, e.g., Alagappan V. et al., Mode compression of transmit and receive arrays for parallel imaging at 7T; ISMRM Book of Abstracts 2008, Toronto, Canada, which is hereby incorporated by reference). Alternatively, each channel can be separately controlled to adjust amplitude and phase via single or multiple RF amplifiers synchronously or asynchronously.

The body coil 13 can be of a single structure or array configuration and can be used for transmitting RF or receiving MRI signals. The body coil 13 can be lined with an acoustic dampening material and/or high permittivity material. The acoustic dampening material is intended to minimize gradient induced eddy currents that cause audio noise due to fast switching of gradient coils. The high permittivity material ($\epsilon_r$ for example of the order of 200-2,000 with very low or zero conductivity [$\sigma$]) aids in focusing the near RF field distribution of the whole body coil 13, thereby minimizing RF power deposition and reducing peak and average specific absorption rate (SAR) values below specified FDA and IEC guidelines. Additionally, SNR is enhanced which can obviate the need for oversampling and thus reduce scan time. The use of saturation RF pulses on areas next to the imaging field of view also can be eliminated, thereby reducing RF power.

Focusing the RF transmit field to a volume confined within the body coil 13 with little or no radiation to volumes outside the body coil 13 effectively shortens the RF coil electrical length and improves performance, providing better transmit and receive efficiencies over the imaging volume. This feature may also allow physically shortening the body coil 13, again improving overall efficiency and subsequent use of a smaller RF amplifier (e.g., 8 KW or less instead of a 12 KW amplifier). The reduction of transmit power depends on the effect a given high permittivity material has on RF coil efficiency based on the anatomy of interest, volume and field strength. Since radiative, resistive and patient losses increase with increasing field strength and frequency, the effect of high dielectric materials may be higher at higher operating frequencies. Likewise, high permittivity material can be used in or near the local coil 10 and patient to reduce SAR and increase SNR of the NMR experiment. Receive signals can be digitized either on the coil or at the magnet or remote from the magnet prior to signal combination. Processing and post-processing can be hosted on an imaging console or on separate consoles.

Scanner electronics can be placed in a 4'×6' area, whereas the imaging operator console can be placed in a 3'×5' area close to the main magnet. Thus the space required for the pediatric sized MRI is well within 15'×15'. Use of virtually cryogen free superconducting magnet design is preferred to reduce weight, overall size including siting considerations.

Neonate imaging sub-system

Figure 2:
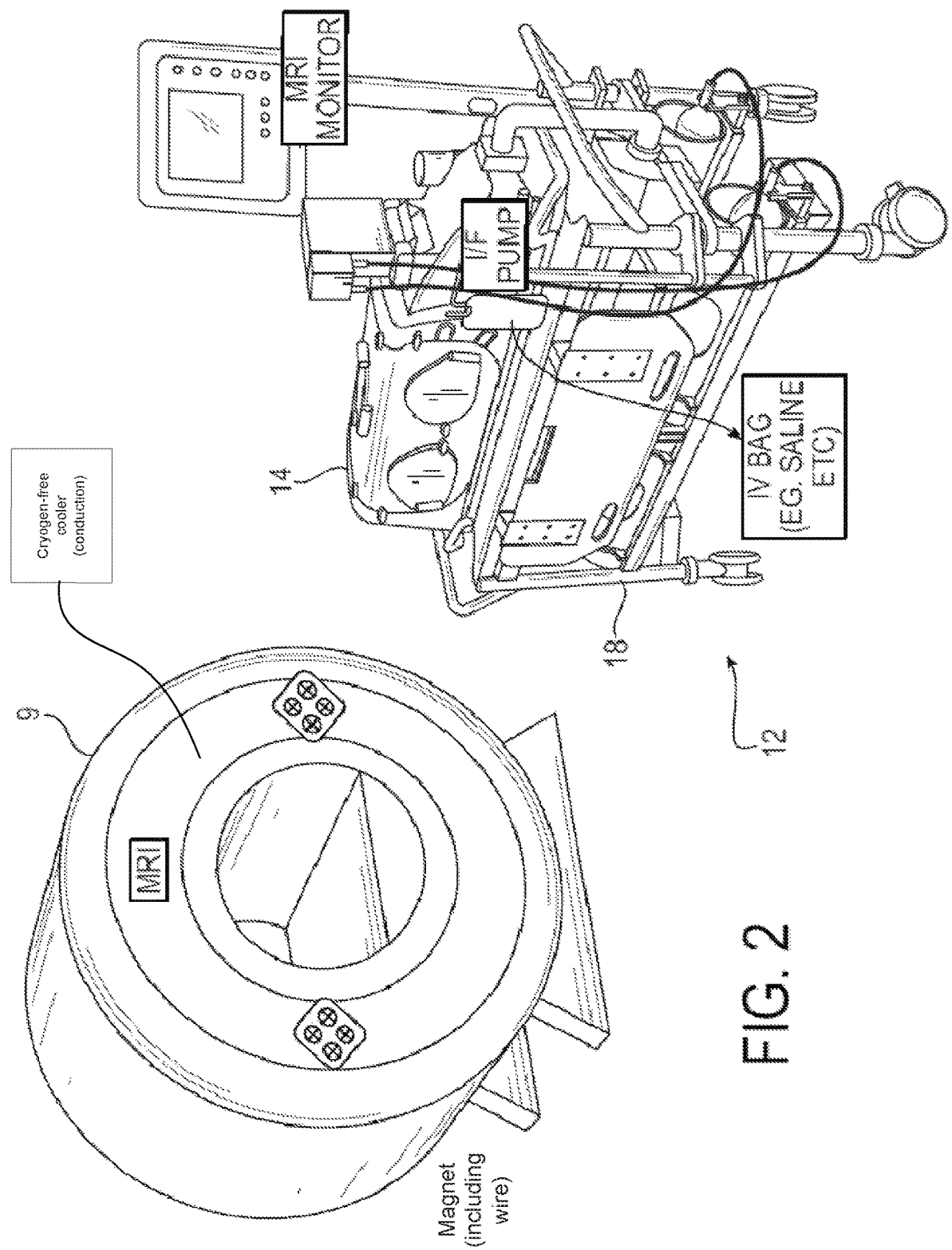
FIG. 2 illustrates an MRI-compatible isolette relative to a magnet of a magnetic resonance imaging system.

Referring now to FIG. 2, an MR compatible neonate imaging sub-system 12 outside a main magnet 9 in accordance with an embodiment of the present disclosure is shown. All of the MRI compatible equipment and accessories (ventilator, monitor, infusion pump, IV bag, oxygen/air tanks, pressure reducers, flow tubes etc.) are mounted on the isolette 14 or trolley 18 and are safe to enter the MRI exam suite, whereas non-magnetic and MR unsafe accessories are removed from the isolette 14 and trolley 18. In the interest of saving gases remaining in the MR conditional tanks, quick connect-disconnects can be provided to switch over between the gas tanks and central hospital gas supply in a matter of seconds.

As described in more detail below, the sub-system 12 includes various components, such as life sustaining equipment, vital signs monitoring equipment, and controlled environment equipment. Additionally, the imaging sub-system 12 can be modular, which facilitates removal and/or installation of various sub-components.

For example, additional or different vital signs monitoring equipment can be easily added to and/or removed from the sub-system 12 via quick release couplings. Generally, such modular components are coupled to the sub-system 12 using hand operable locking clasps, for example. It is contemplated, however, that in some instances it may be preferable to use a relatively more secure coupling means, such as threaded fasteners or the like, to couple a component to the sub-system 12. Furthermore, the modularity of the sub-system 12 facilitates transporting the sub-system to various locations. If a component is not required, it easily can be removed, thus reducing the weight and size of the sub-system.

The entire sub-system 12 is MR compatible, which permits safe and effective radiographic examination of the subject without affecting the isolette performance or the image quality. Moreover, the infant can remain in the isolette 14 during the transport to and from the MR scan room as well as during the MR scan. This facilitates the well-being of the infant, as his/her micro environment is not disturbed. Additionally, life sustaining and monitoring lines can remain coupled to the infant at all times, even during MR scanning.

The imaging system can include an isolette 14 that can be easily removed from the trolley 18 by simply unplugging an electrical cable connector, thereby enabling immediate replacement of the isolette 14 with an already sterile isolette. This rapid isolette swap on/off the trolley 18 permits back-to-back infant imaging studies to be performed without MRI down time, thereby maximizing MRI efficiency.

Figure 3:
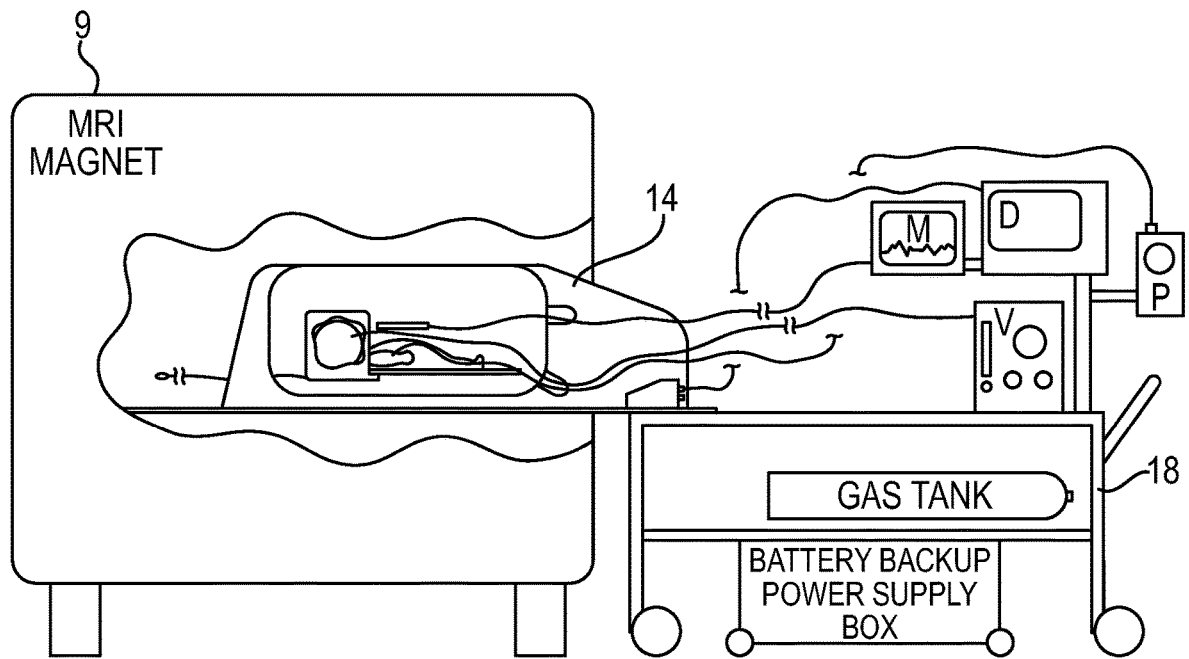
FIG. 3 is a partial-cutaway illustrating an isolette inside a bore of a magnet, and a trolley and accessories (monitor M, user interface/control unit D, ventilator V and infusion pump P) adjacent to the magnet.

With reference to FIG. 3, shown is a diagrammatic view of an isolette, imaging device, diagnostic MRI system assembly with life sustaining and monitoring equipment and accessories. As shown, the patient can be left unperturbed during the MRI examination with continuous monitoring of vital signs and isolette air temperatures via the monitors. A remote ventilator pressure monitor (not shown) can be used as a safety precaution to note when the pressure in the ventilation breathing circuits drops to very low levels. In most cases a whole body coil 13 is used for transmit, whereas the local RF coil array 10 is used for receiving high signal to noise resonance data over the anatomy of interest. In addition to the ventilator, monitor, infusion pumps and IV bags (not shown), MR compatible camera, a temperature control system, functional MRI eye tracking device etc. can be used.

Figure 4:
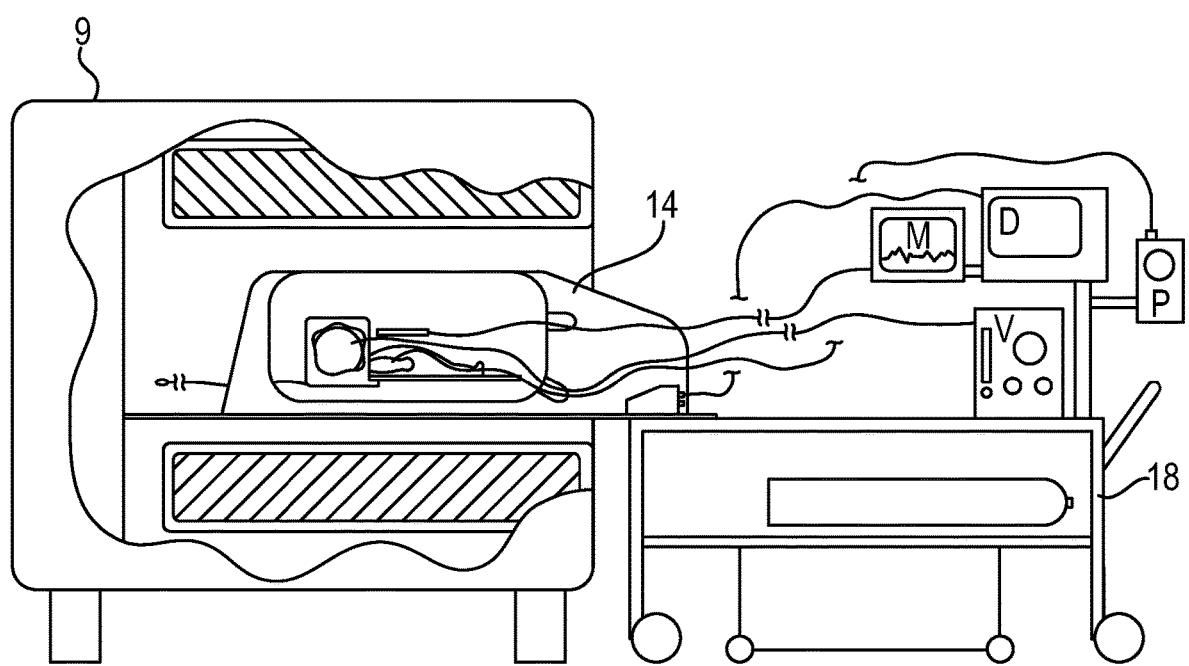
FIG. 4 is a partial-cutaway illustrating an isolette inside a bore of a C-shape magnet, and a trolley and accessories (monitor M, user interface/control unit D, ventilator V and infusion pump P) adjacent to the C-shape magnet.
Figure 5:
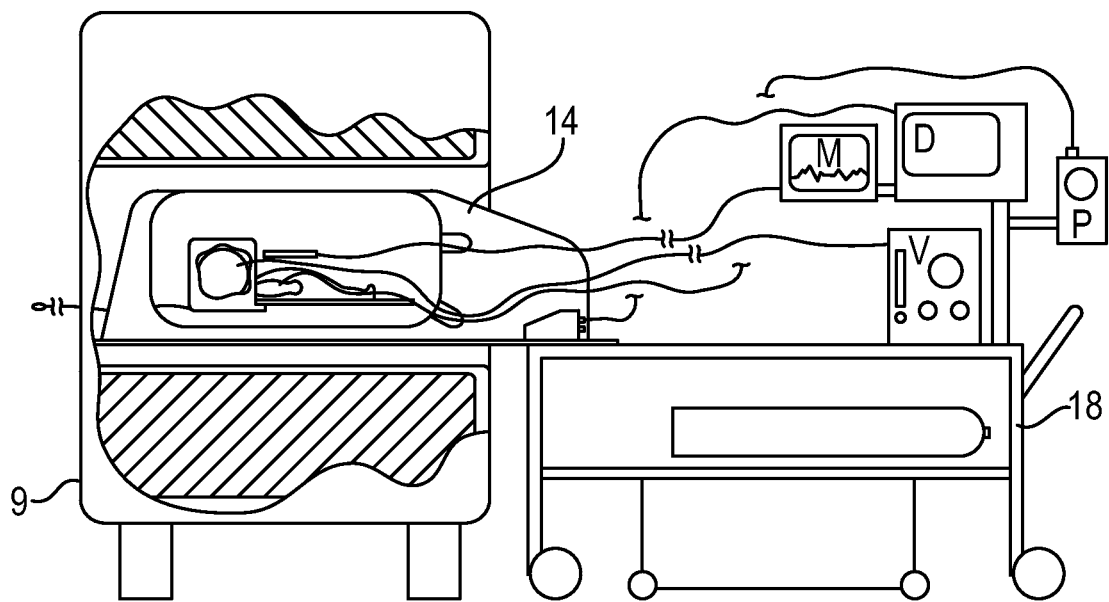
FIG. 5 is a partial-cutaway illustrating an isolette inside a bore of a rectangular-shape magnet, and a trolley and accessories (monitor M, user interface/control unit D, ventilator V and infusion pump P) adjacent to the rectangular shape magnet.
Figure 6:
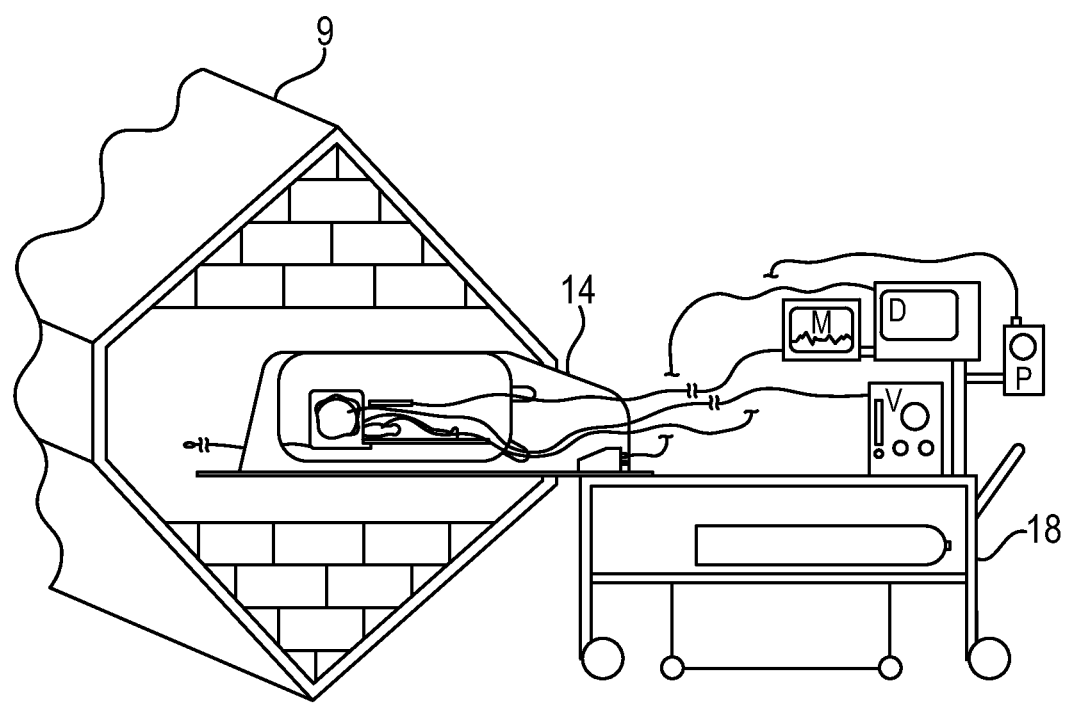
FIG. 6 is a partial-cutaway illustrating an isolette inside a bore of a hexagonal magnet, and a trolley and accessories (monitor M, user interface/control unit D, ventilator V and infusion pump P) adjacent to the hexagonal magnet.

FIGS. 4-6 illustrate other embodiments showing use of the isolette system with other magnet configurations, such as a vertical field "C" shaped magnet configuration using anterior and posterior pole faces (FIG. 4); square, circular or rectangular cross-sectional magnet also using anterior and posterior pole faces with the square or rectangular cross-sections supporting flux return path and shielding (FIG. 5); and hexagonal cross-sectional magnet configuration with anterior and posterior pole faces using the hexagon for the magnetic flux return path, containing the magnet field and shielding (FIG. 6). It is worth noting the introduction of the isolette can be sideways, from the front or both ways with the magnet in the upright directions as shown or tilted sideways. It is noted that the systems shown in FIGS. 3-6 utilize a non-superconducting magnet 9 (in contrast to the system shown in FIG. 2, which utilizes a superconducting magnet 9).

Infant Isolette

Figure 7:
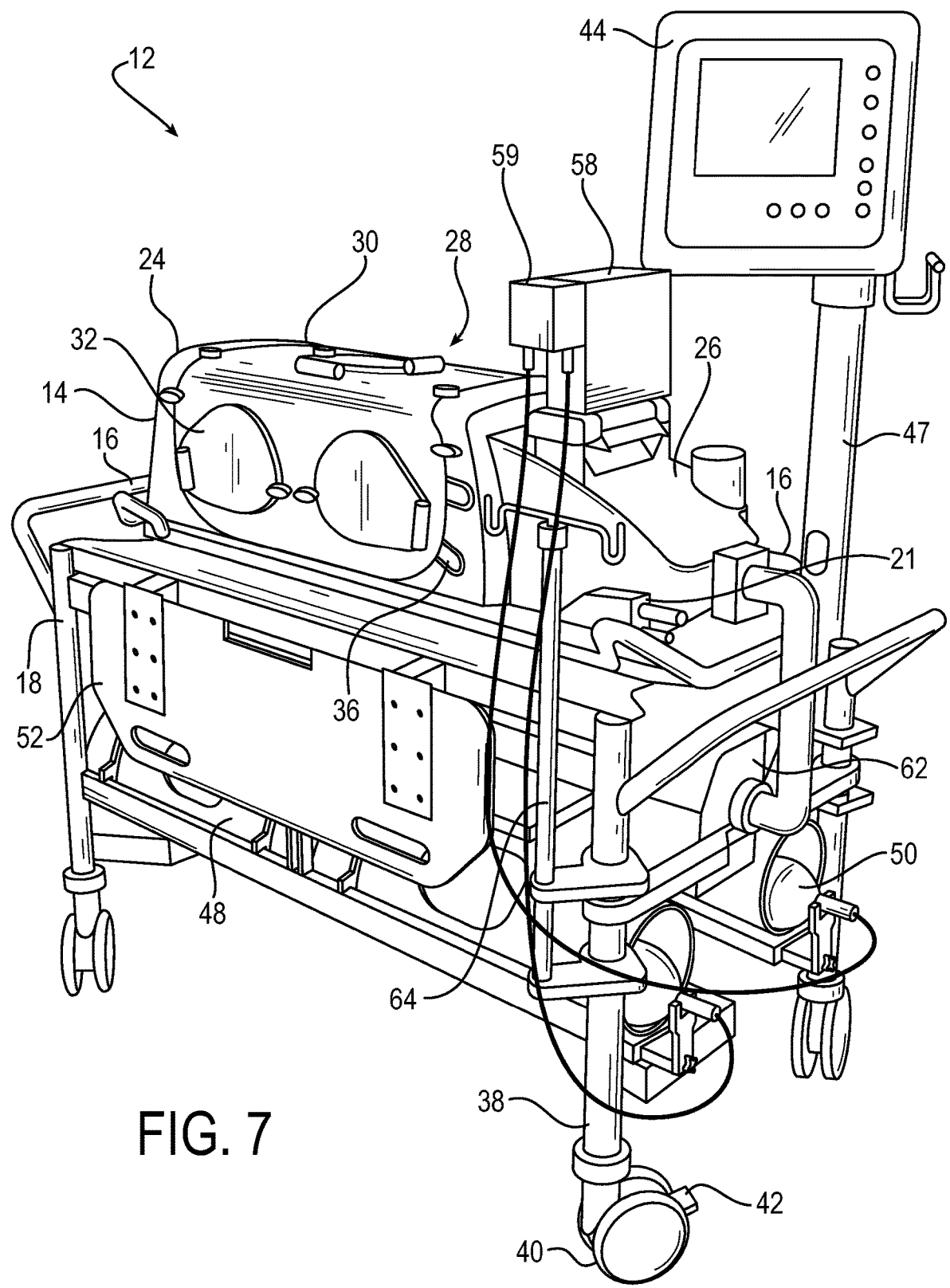
FIG. 7 illustrates an exemplary imaging sub-system including an isolette in accordance with the present disclosure.
Figure 8:
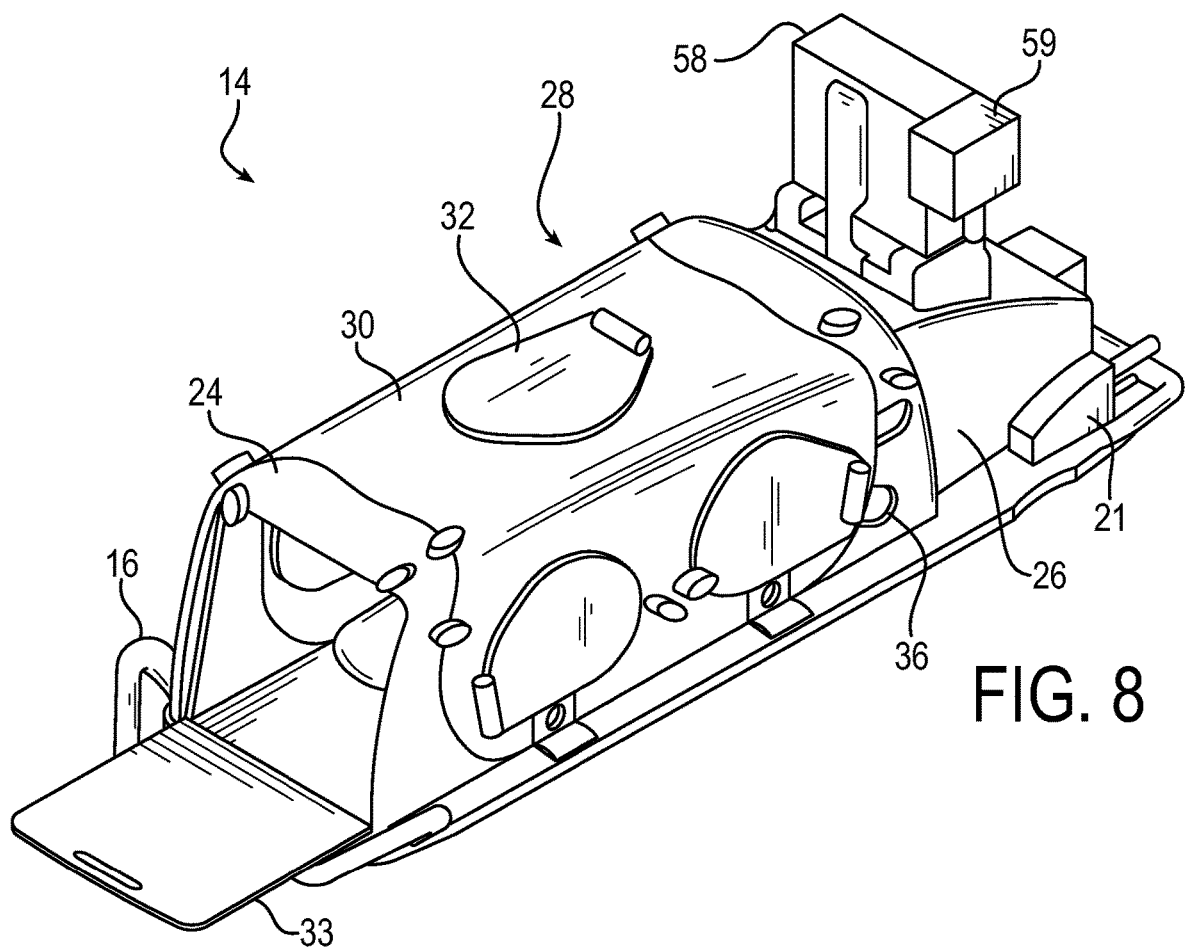
FIG. 8 is a perspective view of an exemplary modular isolette in accordance with the present disclosure.
Figure 9:
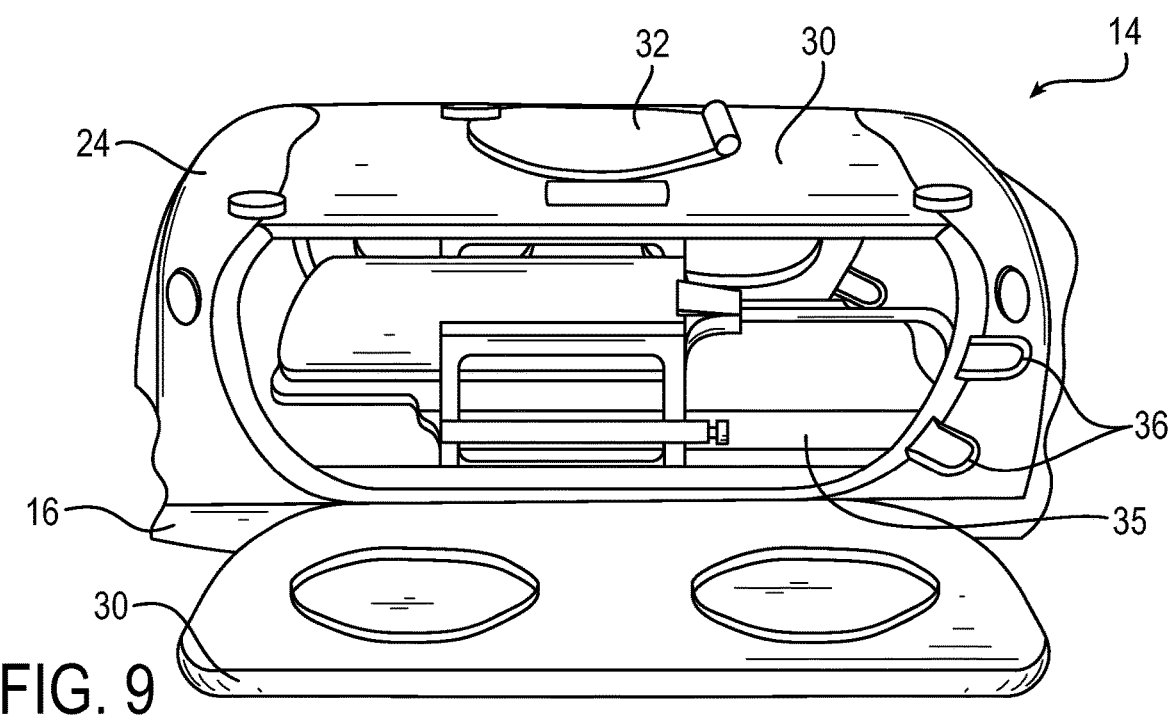
FIG. 9 is a detailed view of the isolette patient section of FIG. 8.

With reference to FIGS. 7-9, an isolette 14 of the neonate imaging subsystem 12 can be formed as a portable, modular unit that, for example, weighs roughly 65 lbs. and is approximately 4 feet long. Assuming two caregivers lifting the isolette, this weight is far below the 50 lbs. per person limit for direct weight lifting according to OSHA standards for a hospital caregiver. The isolette 14 can include ergonomic handles 16 with wide spacing between grips for better balancing and ease of equipment handling by caregivers (e.g., a nurse and/or MR technician during staged transfers between a trolley 18 (FIG. 7) and MR patient table). The isolette 14 is designed to fit flat or curved MR patient tables. The isolette 14 can be powered via a connector 21 that couples power to a high power heater (not shown) and low level sensor cables (which may originate from a control unit).

The isolette 14 can include two sections, a patient section 24 and a heating section 26. The patient section 24 can include a transparent double walled housing 28 that enables complete view of the patient at all times. The patient section 24 can be configured to minimize heat transfer due to convection or radiation. The heating section 26 can receive filtered air, which is forced over a heater (not shown) and enters the patient section 24 on either side of the infant. More particularly, a single ended air supply can be used to minimize the chance of cross-contamination between patients. Fresh air can be drawn in from the ambient environment, for example, from behind a motor 62 through a dust filter followed by a micro-particle clinical filter. A "whisper-wind" technology motor fan design can be used to minimize audio noise within the patient chamber to less than 50 dbA. The air can be drawn through an air channel where it is warmed and humidified via guides on either side of an isolette patient section (e.g., along the entire length of the isolette 14), and the warmed and humidified air can be bled away to the isolette surrounding environment via portals (e.g., portals used for passing patient life sustaining and monitoring lines to the respective equipment and for routing cables for interfacing coils to the MRI). Filtered air can be continuously pushed throughout the isolette 14 and over the infant to eliminate chances of cross-contamination between infants. Filtered air also helps minimize carbon-dioxide ($CO_2$) build up inside the patient section (note larger amounts of $CO_2$ can be deleterious to the subject).

Alternatively, the motor 62 can be located remotely to propel freshly filtered air directionally over a heater and virtually eliminate motor driven audio noise in the patient chamber. For example, a low audible noise technology fan design can be used, which can result in audio noise within the patient chamber being less than 50 dB. Close proximity of the heater to the patient section can provide increased system efficiency, although a remote heater design can be utilized as well. Filtered air can be forced over the heater and inside air channels, which minimize heat loss to environment. Careful adjustment of the channels can balance air flow and temperature inside the patient section within limits well below international performance standards (International Electrotechnical Commission IEC 60601-2-20). Sensor dependent, independent feedback and redundancy can be used in one or more locations throughout the isolette to improve performance, safety and effectiveness. Software and hardware measures can be incorporated to minimize risk while enhancing patient, operator and equipment safety.

A temperature regulator in accordance with the present disclosure, which may be implemented within a control unit, utilizes actual temperature feedback to maintain isolette air temperatures between, for example, 28 to 39 degrees Celsius. Regulation can be based on the air temperature measured in the patient section 24 and/or the air temperature measured in the heating section 26 in combination with the temperature of the ambient surrounding environment and/or or the skin temperature (skin temperature may be continuously monitored at the axilla (under the arm) or preferably the torso). Temperature sensors external to the isolette as well as within the patient section and heater section can be communicatively coupled to the control unit for use in regulating temperature in the patient section. The control unit may include a processor and memory that stores logic that causes the processor to carry out a method of regulating temperature in the isolette in accordance with the present disclosure.

The isolette 14 includes a special ambient mode where based on various parameters as discussed in more detail below, maximum power to the heater is limited and/or interrupted and only freshly filtered air is introduced in the patient section 24. To maintain appropriate temperatures as prescribed by a physician, air temperatures and patient skin temperature are continuously monitored during patient preparation in the intensive care unit, during transport between sections, and during the radiology exam.

The patient section 24 of the isolette 14 can include double-walled doors 30 for complete access on either sides in the case of emergency as well as portals (e.g., hand ports) 32 on all three sides for immediate patient access. The top portal allows administration of substances, such as medications, etc. Also, air pathways and tubes exiting patient airways can be adjusted via the top portal. Portals 32 are also provided at either end of the isolette 14 to enable life sustaining/monitoring lines to be connected to the infant at all times without compromising care and to enable RF coil connections to the MR scanner. An RF coil 10 (FIG. 9), which can be introduced or withdrawn through a door 33 superior to the patient, can slide under a cradle 35 without disturbing the patient inside the isolette 14. The RF coil 10 is described in more detail below with respect to FIG. 11.

Flaps 36 can be provided on rubber gaskets that seal the portals 32, the flaps 36 being designed to hold lines (not shown) extending out of the patient section 24 and connecting to the respective devices. Such flaps 36 enable a clutter-free area around the isolette 14. The flaps 36 can hold the lines during transport and minimize the possibility of such lines being pinched or caught during transport or movement of the isolette 14 and as the isolette 14 is removed from the trolley 18 and/or the MR patient table.

MR Compatible Trolley

Figure 10:
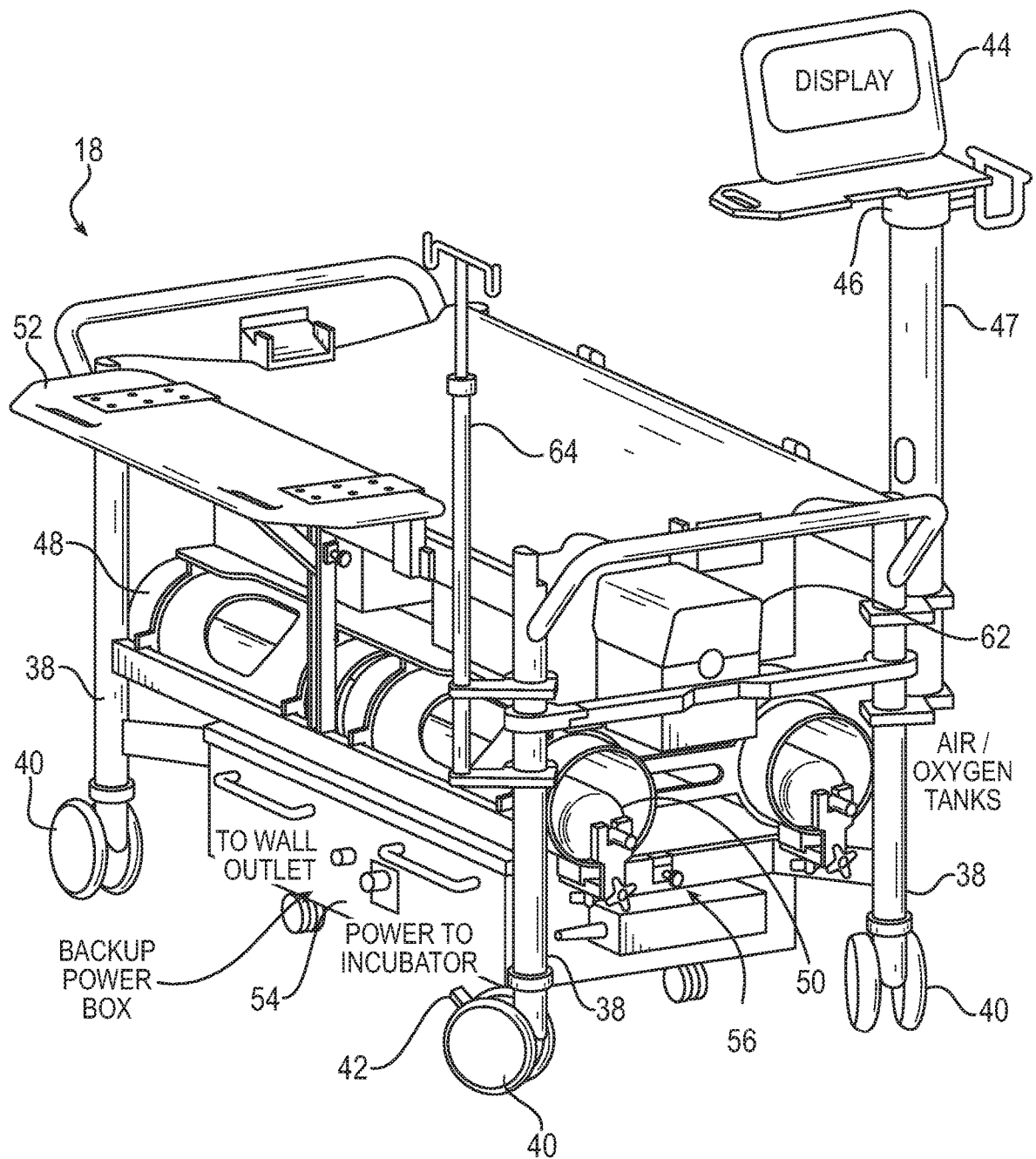
FIG. 10 is a perspective view of an MRI-compatible trolley transfer table that may be used to transport the isolette.

Referring to FIGS. 7 and 10, the exemplary trolley 18 is made of MR compatible material, such as aluminum, for example. The trolley 18, which preferably is contoured to fit narrow hallways and elevator doors in the hospital, can include shock absorbers atop the unit where the isolette 14 is placed. More particularly, shock absorbing struts 38 can be located on all four posts, which rest on freely moving rubber wheels 40. Directional locks (not shown) that aid transport by one caregiver can also be provided. Non-directional locks (or brakes) 42 that restrict trolley motion, for example during transfer of the isolette 14 to/from the MR patient table, during an emergency procedure performed outside of the routine area (e.g., in hallways, elevators, etc.) or during transport (e.g., in a vehicle) can be provided. Accordingly, the trolley 18 can provide shock-free transport of an infant inside the isolette 14 and is robust enough for routine use in a hospital environment (sharp 90 degree bends, wheel chair accessible incline/decline ramps, etc.).

A display/control unit 44 can be located at face height and affixed to a swivel base 46 via post 47 that is attached to the trolley 18. The swivel base 46 enables +/− 120° rotation. A graphic user interface can be displayed on the display/control unit 44, and user interaction can be enhanced with audio and video information (e.g., alarms, etc.). Further, environment isolette control is possible via feedback from temperature sensors located on the sub-system. This helps the isolette 14 adapt to the surrounding temperature without deviating from the stringent operation, performance and safety standards set for medical transport isolettes. Narrow and broad band filtering schemes over the nuclear magnetic resonance (NMR) spectrum, shielded coaxial cables, grounding considerations, etc. are included to reduce EMI/EMC radiation, eliminate undesired harmonics, and minimize risks of high voltage exposure, while maintaining leakage currents below the required IEC guidelines for safe operation of medical equipment.

The trolley 18 can include adjustable restraint mechanisms 48 to accommodate different size oxygen/air tanks 50, e.g., to hold them in place during transport. The trolley 18 can also be designed to accommodate monitoring equipment, infusion pumps, injectors and the like with an easy on/off mechanism (not shown) for enabling/disabling the respective components.

The trolley 18 includes a transfer table 52 that assists with transfer of the isolette 14 to and from the MR patient table. The transfer table 52 extends downward at right angles and locks in to place. In the extended position, the transfer table 52 is supported by the height adjustable MR patient table (not shown), which is designed to bear the weight of the isolette 14 and share the weight bearing between the trolley 18 and the MR patient table. Staged transfer, as opposed to a single transfer sideways swinging motion, is preferred by caregivers and poses less risk to hip twisting while transferring the isolette 14. Note a sliding mechanism (not shown) can be employed that is intended to satisfy zero weight lifting policy adopted by some hospitals. Thus, operator safety is enhanced.

A battery power supply box 54 (FIG. 10), which may be on rollers, slides in and out of trolley guide rails and is held in place via a spring loaded plunger 56. This battery box can be slid out by simultaneously pulling the plunger and handle.

MR Compatible Ventilator

With reference to FIGS. 7 and 8, a MR compatible ventilator 58 with an in-built blender 59 can be used with the isolette 14. The ventilator 58 can be placed atop the isolette 14, over the heating section 26. A ventilator is typically used with patients who have a compromised respiratory system and may not be able to breathe on their own. A blender 59 is used in conjunction with the ventilator to provide a precise mixture of oxygen with air as prescribed by the physician. Input to the blender 59 comes from the oxygen/air tanks 50 whereas, the primary output of the blender 59 is provided to the ventilator 58. The inspiration/expiration rates that vary from patient to patient are set by controls on the ventilator 58, while the flow rate is controlled by the ventilator 58 based on the set rate. The ventilator 58 can be pneumatically driven and hence does not interfere with the performance of the isolette 14 or the MR system.

A backup mechanism can be installed on the ventilator 58 such that in the event the ventilator fails, the user has the option to connect a mechanical aspirator (e.g., a manually pumped balloon) to an auxiliary output of the blender 59 to support the infants breathing. Alternatively, the user also has the option to connect the oxygen/air lines directly to the ventilator 58 or to the infant in the event of blender failure. In all cases, appropriate flow rates are maintained and controlled by pressure reducers, flow tubes and the ventilator 58 to prevent excess flow to the infant. This is important, for example, in patients with encephalopathy in the first few weeks of life, where if excessive oxygen is passed to the patient damage to the eyes (hyperoxia) may occur, or if insufficient oxygen is passed to the infant damage to the brain (hypoxia) can occur. Hence the condition hypoxic-ischemic encephalopathy (HIE), severe HIE in some cases leads to cerebral palsy (CP).

MR Compatible Intravenous I/V Bags

A MR compatible IV pole 64 can be included with the trolley 18. Using MR compatible clips, the MR compatible IV pole 64 enables one or more IV bags to be held atop the trolley 18 close to the MR magnet.

MR Compatible Monitor

Vital signs monitoring is important for the thermoregulatory system compromised infant. Vital signs, such as ECG for measuring heart rate and shape, $SpO_2$ for measuring the patient's oxygen saturation in the blood, NIBP for non-invasively measuring blood pressure, end tidal $CO_2$, which measures the $CO_2$ build up (an increase in $CO_2$ should cause for alarm, high levels of $CO_2$ is deleterious to the health of the subject); skin temperature which serves to monitor the overall status of the patient and its immunity to fight antibodies, etc., can be viewed on the MR compatible monitor/control unit 44. The MR compatible monitor/control unit 44, which does not produce artifacts during an MR scan, can be integral with the isolette 14 or may be a separate unit attached to the trolley 18 as shown in FIG. 10.

MR Compatible Fiber Optic Camera w/Remote Display

An MR compatible fiber optic camera can be used to monitor the infant at all times, especially when the subject is inside the MRI scanner. A remote display can be used inside or outside the MRI scan room for monitoring the infant. Again, care must be ensured that the fiber-optic camera and the display do not interfere with the performance of the isolette or the scanner.

Measures employed in U.S. patent application Ser. No. 10/723,325 filed Nov. 26, 2003 to Srinivasan with regard to the compatibility of the accessory to MR may be applied to the MR infusion pump, injector, ventilator, patient monitor, the display monitor and in general to all electronic items placed in or near the MR magnet.

Custom RF Coil

As noted above, an MR compatible RF coil 10 may be inserted into and removed from the isolette 14 via door 33. The coil 10 can be quickly placed in and out of the isolette 14 by opening the rear door 33 through which the coil 10 is introduced. The coil 10 can be held in place by sliding it under the isolette cradle 35 without disturbing the infant. The coil design incorporates the possibility of the coil being exposed to relatively higher temperatures (up to 39 degrees Celsius), high levels of humidity (of up to 100% rH) and greater levels of oxygen (up to 100%). Thus the coil 10 is designed to withstand the harsh isolette environment without compromising the safety of the experiment and the SNR.

Close proximity of the coil 10 to the subject enhances signal to noise owing to higher filling factors. The coil can be an arrayed coil (multiple coils), which enables parallel (simultaneous) imaging of multiple regions of the patient and can further enhance image quality. This is advantageous in that multiple regions of the infant can be simultaneously imaged, thereby minimizing the time in which the infant must be within the magnet bore. Reducing the time the infant is within the magnet bore also can minimize the possibility of image artifacts, as the shorter imaging time minimizes the chance of infant movement during the imaging process. Parallel transmit capability can lead to even further enhancements over the anatomy of investigation. Other coil combinations, such as a knee coil, head only coil, wrist coil, abdomen coil, etc. can be realized for use with the MRI scanner and the isolette.

Figure 11:
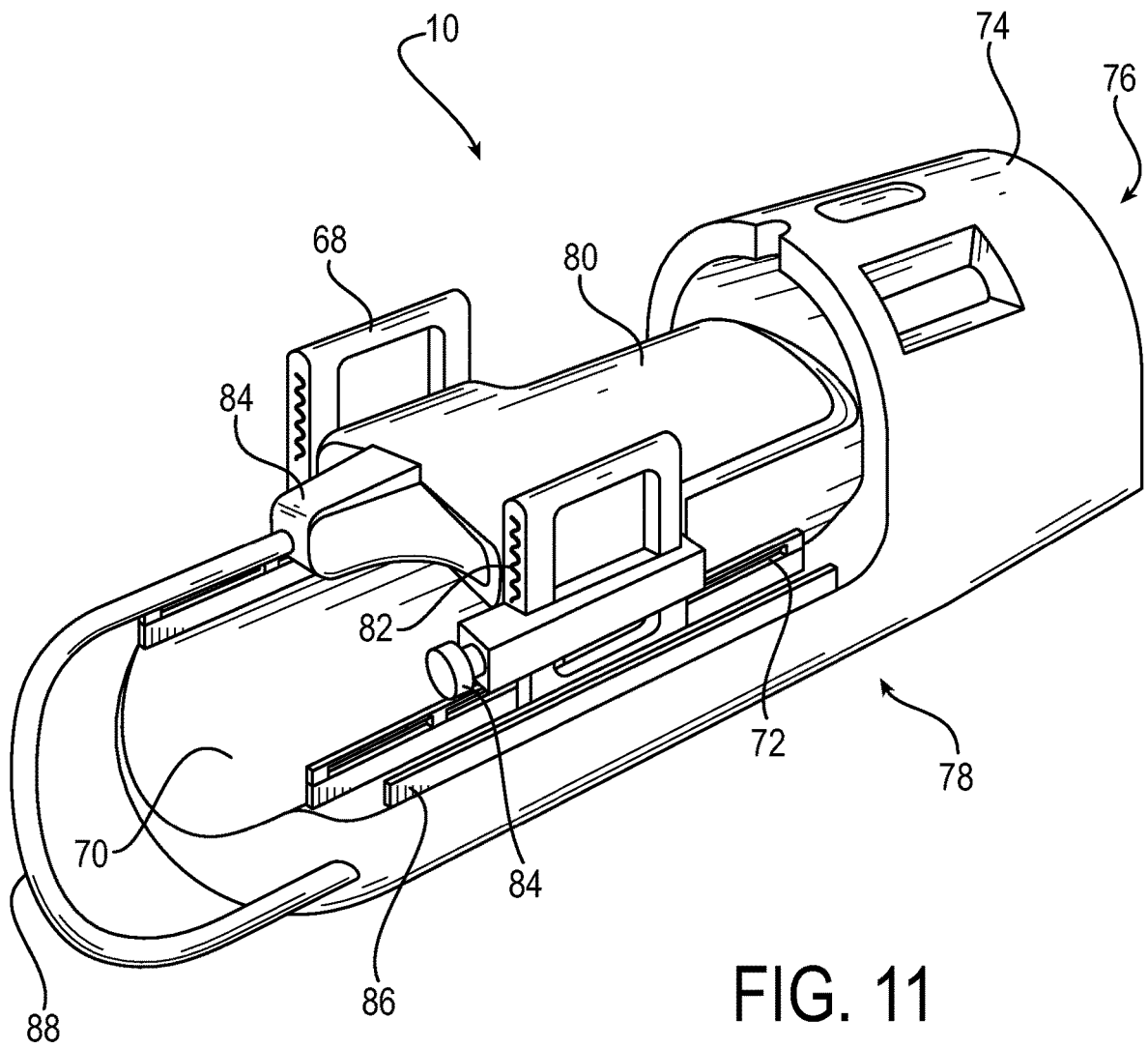
FIG. 11 is a perspective view of a radio frequency coil in accordance with the present disclosure.

With reference to FIG. 11, a custom RF coil array 10 including an infant gantry sub-system 68 can have a curved patient table 70 suited to accommodate $95^{th}$ percentile of the term newborn population up to infants that are up to 12 months old. The table 70 can be concave to center the patient, and a soft cushion (not shown) can be provided for comfort. Slots 72 for forehead and/or body straps can secure the infant during the radiographic procedure. The slots 72 can exist inside a head portion 72 and alongside the entire length of the infant on either side. Foam pads (not shown) may be used over the infant's ear to hold the head still during imaging while reducing audible gradient eddy current induces acoustic noise during the MR scan.

The infant is positioned on the patient table 70 with pads and straps, the infant's head being centered (L-R) inside the head portion 74 of the RF detector array 10 so as to be very close to a closed end 76 (Z direction) of the head portion 74 of the array 10. This ensures maximum coverage over the brain of infant with the head array elements.

Spine coverage can be accomplished with the detector array elements embedded underneath 78 the patient table 70 along the entire length of the patient's spine. Once the patient is placed and secured with pads and straps on the table 70, the anterior infant cardiac array 80 can be introduced. The anterior section 80 can be held on to an adjustable gantry 82 and locked with the mechanical switch 84 (spring loaded, peg or else) whereas the posterior section snaps in place within a slideable holder. Once the respective array sections are secured by their respective holders, the array assembly 80, via rails 86 is slid over the region of interest over the patient (the posterior slides underneath whereas the anterior assembly slides over the rail with groves on either side of the patient table). Note, the anterior section is preferably at its highest point as the array 80 slides over the patient; this is done so as to not touch the patient or dislodge the connections to patient's life sustaining and monitoring devices. Once the anatomical referencing is done by the MR technologist, the anterior section 80 is brought down to the point of being close but not touching or putting weight on the patient' chest or torso. Once the sections are located over the region of interest and the anterior section brought down close to the infant chest or torso, the anterior adjustable gantry 82 is fixed via the mechanical switch 84 (screw or spring based tension or peg). Depending on the examination (head, spine, cardiac, torso, extremity), an MR positioning laser may be centered over a center of the "cocoon" RF coil array 10 and the entire assembly is placed into the magnet isocenter. While the array 80 is positioned for cardiac studies over the patient chest, the face of the patient is clear from the anterior array and can be seen from outside the MR room in the MR technologist area via a camera placed in or near the MR magnet bore. The array 10 is designed to locate output cables 88 arising out of the array in a slot so as to keep them away from the patient, which will eliminate RF burns due to cable proximity to the patient's body.

In summary, the infant array 10 can include two sections (anterior cardiac/torso section, posterior/superior head/spine). The anterior cardiac/torso section connects to the inferior spine section of the patient table and cables flow underneath the patient table to the system receiver. Within the array neighboring (lateral [L-R or cyclic], superior-inferior [H-F]) and diagonal array (X-Y, Y-Z, Z-X) elements are lapped to minimize their mutual inductance to reduce cross-talk and increase combined SNR. Element sizes are appropriately chosen to cover the brain, spine, heart, abdomen, extremity in $95^{th}$ percentile of newborn population and infants up to 6 months.

Each element is interfaced to an individual preamplifier to boost SNR as SNR of the entire chain is dependent on the first stage of the receiver. Outputs from the preamplifiers of the array sections (head, spine, anterior cardiac/torso, etc.) are routed through a RF shield to the system receiver. To break the circulating RF currents in this RF shield and to minimize the interaction of the cable with the patient, several RF transformers (or baluns or cable traps) are introduced at equal to or less than quarter wavelength distance at the NMR frequency to isolate adjacent sections of the cables between transformers. This drastically reduces the interaction of the cable to the patient and helps prevent RF burns generally caused due to close proximity of the cable to the patient at high incident RF during a MR scan.

Temperature Control

Figure 12:
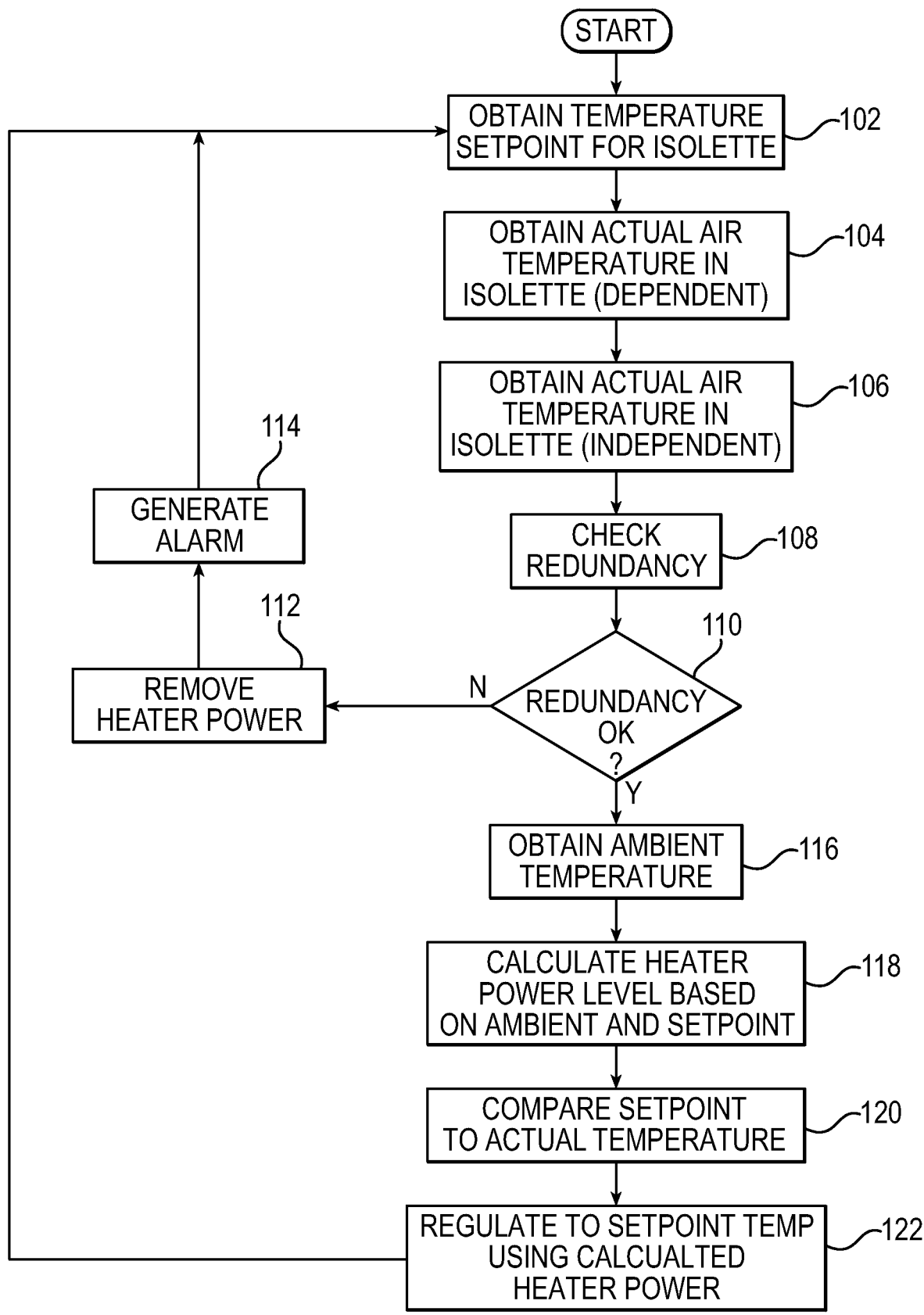
FIG. 12 is a flow chart illustrating an exemplary method for controlling temperature in an isolette in accordance with the present disclosure.

Referring now to FIG. 12, illustrated is a flow chart illustrating steps for an exemplary method for controlling temperature within an isolette 14 in accordance with the present disclosure. The flow chart includes a number of process blocks arranged in a particular order. As should be appreciated, many alternatives and equivalents to the illustrated steps may exist and such alternatives and equivalents are intended to fall within the scope of the claims appended hereto. Alternatives may involve carrying out additional steps or actions not specifically recited and/or shown, carrying out steps or actions in a different order from that recited and/or shown, and/or omitting recited and/or shown steps. Alternatives also include carrying out steps or actions concurrently or with partial concurrence.

Beginning at step 102, a temperature setpoint for the isolette 14 is obtained. Such temperature setpoint may be specified by a physician and entered, for example, via a user interface or the like. Next at steps 104 and 106 the actual air temperature within the isolette 14 is obtained. In accordance with a preferred embodiment, the actual air temperature is obtained using at least two temperature sensors, where a first temperature sensor may be used to regulate the temperature within the isolette 14 while a second temperature sensor may be used for redundancy purposes.

For example, at steps 108 and 110 a redundancy check can be performed where the temperature reading obtained from the first temperature sensor is compared to the temperature reading obtained from the second temperature sensor. If the temperature readings between the first and second sensors are not within the acceptable range or not within a prescribed tolerance value, the method moves to step 112 where power to the heater 26 is removed. For example, power may be provided to the heater 26 via a switching device. If the redundancy check fails, the control unit can command the switch to open, thereby removing power from the heater 26. Next at step 114 an alarm may be generated to notify a nurse or physician that there is a problem with one or both of the temperature sensors, and then the method moves back to step 102.

Moving back to step 110, if the redundancy check passes (e.g., the temperature reading of the first and second sensors are within a prescribed range and/or tolerance value of each other), the method moves to step 116 where the ambient temperature outside of the isolette 14 is obtained via a third temperature sensor. At step 118, the measured ambient temperature is used to calculate a power level for the heater.

For example, the measured ambient temperature may be compared to a base-line ambient temperature. If the measured ambient temperature is greater than the base-line ambient temperature, then the maximum power supplied to the heater 26 may be limited (e.g., the maximum current provided to heating element can be limited to lower the maximum possible heat output by the heating element) as the warmer ambient requires less work from the heater 26. Conversely, if the actual ambient temperature is less than the base-line ambient temperature then the maximum power supplied to the heater 26 can be increased (e.g., the maximum current provided to the heating element can be increased to increase the maximum heat output by the heating element) as the colder ambient requires more work from the heater 26. An exemplary equation for determining the maximum power provided to the heater is provided in Equation 1, where Hp is the calculated maximum heater power, Tb is the base-line ambient temperature, Ta is the actual ambient temperature, and Pr is the regulated power of the heater.

$$Hp = Tb/Ta * Pr \qquad \text{Equation 1}$$

It is worth noting, other complex equations can be realized depending on the intended application.

Figure 13:
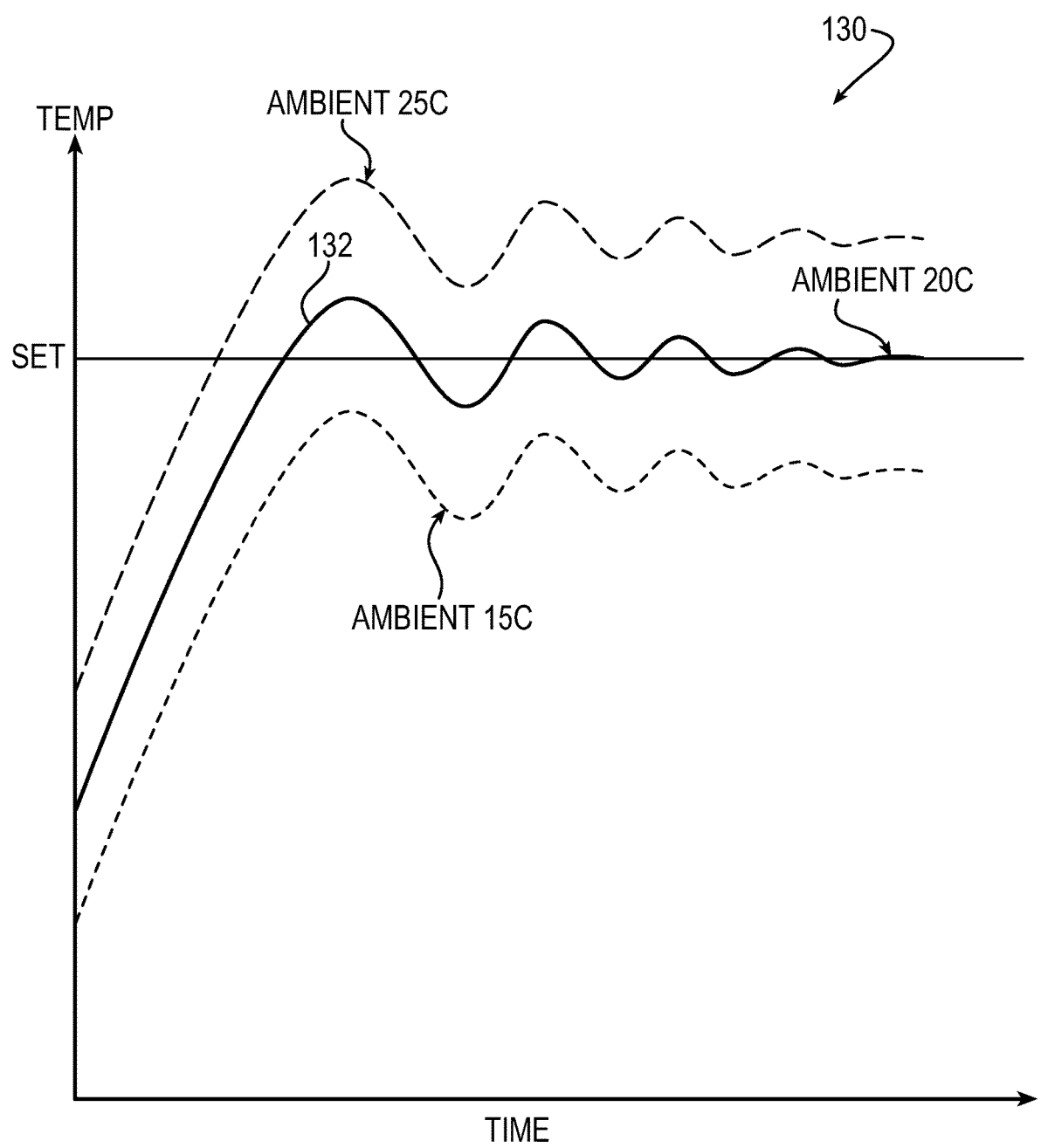
FIG. 13 is a graph showing temperature response within the isolette due to different ambient conditions.

With additional reference to FIG. 13, by regulating the maximum power provided to the heater 26 a heat-rise curve 130 can be made to coincide with that of a baseline value 132. Such maximum heater power regulation is beneficial to minimize the likelihood of overheating due to ambient environments having elevated temperatures, and to minimize the likelihood of insufficient heating in ambient environments with lower temperatures.

Next at step 120 the temperature setpoint as obtained at step 102 is compared to the measured temperature within the isolette 14 as obtained at step 104, and at step 122 the heater 26 is commanded to increase or decrease heat output so as to regulate the isolate temperature. Steps 120 and 122 may be implemented as a PID controller or the like that is executed by the control unit.

Accordingly, the regulation method regulates not only the maximum power supplied to the heater, but also the heat output provided by the heater. By regulating the maximum power supplied to the heater independent of a commanded heat output from the heater, temperature regulation within the isolette 14 is improved, particularly when the isolette 14 is transferred from one ambient environment to another. Such regulation is also beneficial to maintain adequate heating power (and thus prevent over heating) when the doors 30 or 33 and/or portals 32 are left open for extended periods of time.

The system in accordance with the present disclosure enables seamless transfer of a patient. For example, the patient remains in an undisturbed, disinfected environment throughout the MRI exam. The trolley 18 can be part of the MRI patient table or otherwise support the isolette 14 along with all of the life sustaining and monitoring equipment and accessories. The isolette 14 atop the trolley 18 can be slid in to the magnet bore and yet not come in direct contact with the bore, alleviating any risk of contamination from a foreign body. The disinfected high SNR imaging device is introduced without disturbing the sick infant. Further, modular isolette system design enables quick replacement on and off the trolley and the MR patient table. Efforts to place the patient in an isolette section and transfer to the MRI and use the extendable/retractable design or operate isolette together with the MRI magnet 9 or the traditional incubator are non-practical options subject to contamination not recommended by hospital caregivers.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

What is claimed is:

1. A pediatric magnetic resonance imaging (MRI) system, comprising:
   a super conducting magnet comprising wire;
   an isolette including a patient section for accommodating a patient, the isolette positionable relative to the magnet;

a radio frequency (RF) array positonable within the patient section of the isolette, the RF array comprising a plurality of coils configured for simultaneous imaging of different portions of a patient, the plurality of coils being distinct from one another, the RF array comprising a patient support section including a support surface for supporting the patient and an enclosed portion for receiving a head of the patient, the enclosed portion and the patient support section formed as a unitary construction, wherein a first coil is arranged over the support section, a second coil is arranged within the support section, and a third coil is arranged within the enclosed portion, the first, second and third coils integrated in a common structure;

a cooling system for controlling a temperature of the wire;

wherein the MRI system further comprises;

a gantry movably coupled to the support section; and the first coil of the plurality of coils is coupled to the gantry, the first coil, via the gantry, movable relative to the support section in at least two degrees of freedom.

2. The MM system according to claim 1, wherein the magnet comprises wire formed from magnesium diboride (MgB$_2$).

3. The MRI system according to claim 1, wherein the first coil is movable along alongitudinal axis of the support section.

4. The MRI system according to claim 1, wherein the first coil is movable in elevation relative to the support section.

5. The MRI system according to claim 1, wherein the cooling system is operative to maintain a temperature of the wire between 8-12 degrees K.

6. The MRI system according to claim 1, wherein the cooling system comprises a conduction cooling system.

7. The MRI system according to claim 1, wherein the RF array comprises a high-permittivity material.

8. The MRI system according to claim 7, wherein the high-permittivity material has a permitivitty between 200 and 2000.

9. The MM system according to claim 7, wherein a conductivity of the high-permitivitty material is 0.

10. The MRI system according to claim 1, wherein the first, second and third coils of the RF array are connected to the patient support section, and movement of the support section causes corresponding movement of the first, second and third coils.

11. The MRI system according to claim 1, wherein the second coil is embedded within the patient support section.

12. The MRI system according to claim 1, wherein the first coil is configured to image a torso region of the patient, the second coil is configured to image a spine region of the patient, and the third coil is configured to image a head region of the patient.

13. The MRI system according to claim 1, wherein the cooling system is cryogen-free.

14. The MRI system according to claim 1, wherein the cooling system is substantially helium-free.

15. The MRI system according to claim 1, wherein the support section and the enclosed portion are non-movable relative to each other.

16. A pediatric magnetic resonance imaging (MRI) radio frequency (RF) coil array, comprising:

a patient support section including a support surface for supporting a patient to be imaged;

an enclosed portion for receiving a head of the patient to be imaged, the enclosed portion and the patient support section formed as a unitary construction;

a gantry movably coupled to the support section; and a plurality of coils configured for simultaneous imaging of different portions of a patient, the plurality of coils being distinct from one another, wherein a first coil of the plurality of coils is coupled to the gantry and arranged over the support section, the first coil, via the gantry, movable relative to the support section in at least two degrees of freedom to enable imaging of a patient arranged between the first coil and the patient support section, a second coil of the plurality of coils is arranged within the support section, and a third coil of the plurality of coils is arranged within the enclosed portion, the first, second and third coils integrated in a common structure.

17. The RF coil array according to claim 16, wherein the patient support section and the enclosed section are non-movable fixed relative to each other.

18. The RF coil array according to claim 16, wherein the gantry is movable along a longitudinal axis of the support section.

19. The RF coil according to claim 16, wherein the gantry is movable in elevation relative to the support section.

* * * * *